(12) United States Patent
Miraki et al.

(10) Patent No.: US 8,500,757 B2
(45) Date of Patent: Aug. 6, 2013

(54) SURGICAL PUNCTURE CINCH AND CLOSURE SYSTEM

(75) Inventors: Manouchehr Miraki, Laguna Hill, CA (US); Yoon H. Kwon, Mission Viejo, CA (US); Frank Nguyen, Westminster, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 201 days.

(21) Appl. No.: 12/844,139

(22) Filed: Jul. 27, 2010

(65) Prior Publication Data

US 2011/0028995 A1 Feb. 3, 2011

Related U.S. Application Data

(60) Provisional application No. 61/229,190, filed on Jul. 28, 2009, provisional application No. 61/252,114, filed on Oct. 15, 2009.

(51) Int. Cl.
*A61B 17/04* (2006.01)

(52) U.S. Cl.
USPC .......................................... 606/144; 606/139

(58) Field of Classification Search
USPC .................. 606/139, 144, 146, 148, 222–227
See application file for complete search history.

(56) References Cited

U.S. PATENT DOCUMENTS

| | | |
|---|---|---|
| 67,545 A | 8/1867 | Hodgins |
| 2,008,251 A | 7/1935 | Hillebrand |
| 2,737,954 A | 3/1956 | Knapp |
| 3,638,653 A | 2/1972 | Berry |
| 4,011,873 A | 3/1977 | Hoffmeister |
| 4,204,541 A | 5/1980 | Kapitanov |
| 4,345,601 A | 8/1982 | Fukuda |
| 4,595,007 A | 6/1986 | Mericle |
| 4,605,002 A | 8/1986 | Rebuffat |
| 4,683,885 A | 8/1987 | Hutterer et al. |
| 5,018,530 A | 5/1991 | Rank et al. |
| 5,188,636 A | 2/1993 | Fedotov |
| 5,269,791 A | 12/1993 | Mayzels et al. |
| 5,304,184 A | 4/1994 | Hathaway et al. |
| 5,320,632 A | 6/1994 | Heidmueller |

(Continued)

FOREIGN PATENT DOCUMENTS

| | | |
|---|---|---|
| DE | 4304353 | 4/1994 |
| EP | 2078498 | 7/2009 |

(Continued)

*Primary Examiner* — Darwin Erezo
*Assistant Examiner* — Robert A Lynch
(74) *Attorney, Agent, or Firm* — Guy L. Cumberbatch; Ryan E. Lindsey (57) ABSTRACT

A system for forming a purse string suture, including a suture applicator having a proximal handle, a length of suture wound on a spool, and a hollow suture needle extending from a distal end of the handle. The suture needle projects distally from the handle in a helical shape and terminates in a sharp distal tip with an opening in one side close to the distal tip. A free end of the length of suture may extend out of the distal tip and back into the hollow suture needle through the opening. The suture needle may have a deflection segment adjacent the distal tip that is more flexible than the rest of the helical distal portion of the suture needle. A linear hollow pivot shaft extends from a distal end of the handle substantially along an axis of the helical distal portion of the suture needle.

13 Claims, 9 Drawing Sheets

U.S. PATENT DOCUMENTS

| | | | |
|---|---|---|---|
| 5,330,503 A | 7/1994 | Yoon | |
| 5,353,800 A * | 10/1994 | Pohndorf et al. | 600/486 |
| 5,356,424 A | 10/1994 | Buzerak et al. | |
| 5,364,408 A | 11/1994 | Gordon | |
| 5,368,601 A | 11/1994 | Sauer et al. | |
| 5,374,275 A | 12/1994 | Bradley et al. | |
| 5,403,329 A | 4/1995 | Hinchcliffe | |
| 5,405,376 A | 4/1995 | Mulier et al. | |
| 5,417,699 A | 5/1995 | Klein et al. | |
| 5,417,700 A | 5/1995 | Egan | |
| 5,425,737 A | 6/1995 | Burbank et al. | |
| 5,431,666 A | 7/1995 | Sauer et al. | |
| 5,454,834 A | 10/1995 | Boebel et al. | |
| 5,476,470 A | 12/1995 | Fitzgibbons, Jr. | |
| 5,527,322 A | 6/1996 | Klein et al. | |
| 5,545,148 A | 8/1996 | Wurster | |
| 5,562,685 A | 10/1996 | Mollenauer et al. | |
| 5,573,540 A | 11/1996 | Yoon | |
| 5,582,616 A | 12/1996 | Bolduc et al. | |
| 5,695,462 A | 12/1997 | Sutcu et al. | |
| 5,700,273 A | 12/1997 | Buelna et al. | |
| 5,709,692 A | 1/1998 | Mollenauer et al. | |
| 5,792,152 A | 8/1998 | Klein et al. | |
| 5,810,850 A | 9/1998 | Hathaway et al. | |
| 5,810,851 A | 9/1998 | Yoon | |
| 5,810,882 A | 9/1998 | Bolduc et al. | |
| 5,820,631 A | 10/1998 | Nobles | |
| 5,836,955 A | 11/1998 | Buelna et al. | |
| 5,846,253 A | 12/1998 | Buelna et al. | |
| 5,891,159 A | 4/1999 | Sherman et al. | |
| 5,935,138 A | 8/1999 | McJames, II et al. | |
| 5,947,983 A | 9/1999 | Solar et al. | |
| 5,972,005 A | 10/1999 | Stalker et al. | |
| 6,074,404 A | 6/2000 | Stalker et al. | |
| 6,143,004 A | 11/2000 | Davis et al. | |
| 6,203,554 B1 | 3/2001 | Roberts | |
| 6,206,893 B1 | 3/2001 | Klein et al. | |
| 6,296,656 B1 | 10/2001 | Bolduc et al. | |
| 6,315,784 B1 | 11/2001 | Djurovic | |
| 6,454,777 B1 | 9/2002 | Green | |
| 6,493,591 B1 * | 12/2002 | Stokes | 607/127 |
| 6,514,263 B1 | 2/2003 | Stefanchik et al. | |
| 6,517,553 B2 | 2/2003 | Klein et al. | |
| 6,626,917 B1 | 9/2003 | Craig | |
| 6,663,633 B1 | 12/2003 | Pierson, III | |
| 6,723,107 B1 | 4/2004 | Skiba et al. | |
| 6,837,893 B2 | 1/2005 | Miller | |
| 6,884,248 B2 | 4/2005 | Bolduc et al. | |
| 6,986,776 B2 | 1/2006 | Craig | |
| 7,011,682 B2 * | 3/2006 | Lashinski et al. | 623/2.37 |
| 7,060,077 B2 | 6/2006 | Gordon et al. | |
| 7,077,850 B2 | 7/2006 | Kortenbach | |
| D543,626 S | 5/2007 | Watschke et al. | |
| 7,323,004 B2 | 1/2008 | Parihar | |
| 7,361,180 B2 * | 4/2008 | Saadat et al. | 606/139 |
| 7,371,244 B2 | 5/2008 | Chatlynne et al. | |
| 7,377,926 B2 | 5/2008 | Topper et al. | |
| 7,618,427 B2 | 11/2009 | Ortiz et al. | |
| 7,637,918 B2 | 12/2009 | Dant | |
| 7,699,892 B2 | 4/2010 | Rafiee et al. | |
| 7,704,269 B2 | 4/2010 | St. Goar et al. | |
| 2002/0147456 A1 * | 10/2002 | Diduch et al. | 606/144 |
| 2004/0147957 A1 | 7/2004 | Pierson, III | |
| 2004/0176802 A1 | 9/2004 | Skiba et al. | |
| 2005/0033323 A1 | 2/2005 | Kim | |
| 2006/0036265 A1 | 2/2006 | Dant | |
| 2006/0074484 A1 | 4/2006 | Huber | |
| 2006/0237022 A1 | 10/2006 | Chen et al. | |
| 2007/0112422 A1 | 5/2007 | Dehdashtian | |
| 2007/0149987 A1 | 6/2007 | Wellman et al. | |
| 2007/0203479 A1 | 8/2007 | Auth et al. | |
| 2007/0203506 A1 | 8/2007 | Sibbitt et al. | |
| 2008/0033459 A1 | 2/2008 | Shafi et al. | |
| 2008/0051807 A1 | 2/2008 | St. Goar et al. | |
| 2008/0140091 A1 | 6/2008 | DeDeyne et al. | |
| 2008/0188873 A1 | 8/2008 | Speziali | |
| 2009/0082788 A1 | 3/2009 | ElMaraghy | |
| 2009/0099578 A1 | 4/2009 | Heneveld et al. | |
| 2009/0240264 A1 | 9/2009 | Tuval et al. | |

FOREIGN PATENT DOCUMENTS

| | | |
|---|---|---|
| WO | 9413211 A1 | 6/1994 |
| WO | 9716121 | 5/1997 |
| WO | 9804195 | 2/1998 |
| WO | 2005112789 A2 | 12/2005 |
| WO | 2006063481 | 6/2006 |
| WO | 2006116558 | 11/2006 |
| WO | 2007098212 | 8/2007 |
| WO | 2008076548 A2 | 6/2008 |
| WO | 2009116042 | 9/2009 |
| WO | 2010011777 | 1/2010 |
| WO | 2010048427 | 4/2010 |

* cited by examiner

SURGICAL PUNCTURE CINCH AND CLOSURE SYSTEM

RELATED APPLICATION DATA

The present application claims priority under 35 U.S.C. §119(e) to U.S. Provisional Applications No. 61/229,190 filed Jul. 28, 2009 and No. 61/252,114 filed Oct. 15, 2009.

FIELD OF THE INVENTION

The present invention relates to methods and systems for cinching a tissue puncture around an implement and closing the puncture after removal of the implement, in particular for punctures in heart tissue.

BACKGROUND OF THE INVENTION

The heart is a hollow muscular organ of a somewhat conical form; it lies between the lungs in the middle mediastinum and is enclosed in the pericardium. The heart rests obliquely in the chest behind the body of the sternum and adjoining parts of the rib cartilages, and typically projects farther into the left than into the right half of the thoracic cavity so that about one-third is situated on the right and two-thirds on the left of the median plane. The heart is subdivided by septa into right and left halves, and a constriction subdivides each half of the organ into two cavities, the upper cavity being called the atrium, the lower the ventricle. The heart therefore consists of four chambers; the right and left atria, and right and left ventricles, with one-way flow valves between respective atria and ventricles and at the outlet from the ventricles.

Heart valve replacement may be indicated when there is a narrowing of a native heart valve, commonly referred to as stenosis, or when the native valve leaks or regurgitates, such as when the leaflets are calcified. When replacing the valve, the native valve may be excised and replaced with either a biologic or a mechanical valve.

Conventional heart valve surgery is an open-heart procedure conducted under general anesthesia, and is a highly invasive operation. The first 2-3 days following surgery are spent in an intensive care unit where heart functions can be closely monitored. The average hospital stay is between 1 to 2 weeks, with several more weeks to months required for complete recovery.

In recent years, advancements in minimally-invasive surgery and interventional cardiology have encouraged some investigators to pursue percutaneous replacement of the aortic heart valve. Percutaneous Valve Technologies ("PVT"), formerly of Fort Lee, N.J. and now part of Edwards Lifesciences of Irvine, Calif., has developed a plastically- or balloon-expandable stent integrated with a bioprosthetic valve. The stent/valve device, now called the Edwards Sapien™ Heart Valve, is deployed across the native diseased valve to permanently hold the valve open, thereby alleviating a need to excise the native valve. The Edwards Sapien™ Heart Valve is designed for delivery with the RetroFlex™ delivery system in a cardiac catheterization laboratory under local anesthesia using fluoroscopic guidance, thereby avoiding general anesthesia and open-heart surgery.

Some researchers propose implanting prosthetic heart valves at the aortic annulus using a direct-access transapical (through the left ventricular apex) approach (e.g., U.S. Patent Publication No. 2006-0074484). The left ventricular apex LVA is directed downward, forward, and to the left (from the perspective of the patient). The apex typically lies behind the fifth left intercostal space (or between the fourth and fifth), 8 to 9 cm from the mid-sternal line, and about 4 cm below and 2 mm to the medial side of the left mammary papilla. Access to the left ventricle may therefore be attained through an intercostal incision positioned over the fifth left intercostal space. Such an approach is often termed a "mini-thoracotomy," and lends itself to surgical operations on the heart carried out using one or more short tubes or "ports"—thus, the operations are often referred to as "port-access" procedures.

Dehdashtian in U.S. Patent Publication No. 2007-0112422 discloses a port-access delivery system for transapical delivery of a prosthetic heart valve including a balloon catheter having a steering mechanism thereon that passes through an access device such as an introducer. The surgeon forms a puncture in the apex with a needle, advances a guidewire, then a dilator, and finally the introducer. Purse string sutures are pre-installed around the puncture to seal against blood leakage around the various devices and provide a closure after the procedure. During the procedure the doctor/assistant is able to apply tension to the purse-string-suture, which prevents inadvertent blood loss. After the deployment of the heart valve, the purse sting-suture is then used to permanently close the opening of the heart by drawing concentric tension on the suture ends, and tying a secure knot. The aforementioned Edwards Sapien™ Heart Valve may be inserted transapically with the Ascendra™ delivery system, much like the system disclosed in Dehdashtian.

Purse string sutures are often affixed to the heart, major arteries, and/or major veins to permit secure placement of tubes for cardiopulmonary bypass (CPB), for instance. Specifically, purse string sutures are used to seal the tissue around a cannula placed within the cardiac tissue. A purse string suture usually consists of a synthetic filament placed in a circular pattern, which is secured by taking four to five bites of tissue placed at uniform intervals around a tube, for example, from positions (with respect to a 12-hour clock face) at 1:00 to 2:00, 4:00 to 5:00, 7:00 to 8:00, and 10:00 to 11:00. Two concentric sutures usually are employed in the event that one suture breaks, and to help minimize bleeding around the surgically inserted tube. If blood pressure is not excessively high, a single purse string suture can be employed. When the tube is removed at the end of the procedure, the two ends of each suture filament are tied together to produce a water-tight seal.

Installation of the purse string sutures may be somewhat time-consuming. Also, this procedure is often performed on elderly patients, where the tissue of the heart is friable and may hold sutures poorly. Consequently, when the doctor/assistant applies tension to the purse string-suture there may be a possibility that the tissue will tear.

Despite known techniques for sealing tissue punctures in port-access procedures, improved methods and apparatuses that are more robust and even less invasive are needed.

SUMMARY OF THE INVENTION

The present application provides a system for delivery of a prosthetic (i.e., replacement) heart valve to a native valve site without an open chest procedure, with a purse string suture applied to the heart to seal the tissue around ports passed therethrough and/or to seal any punctures in the heart wall. More specifically, the present application describes several devices for automatically installing purse string sutures around direct-access ports (or other access instruments) for sealing against blood loss and closing the puncture after removal of the port. More broadly, the suture applicator systems described herein may be utilized in the context of various cardiac and other surgeries that benefit from a purse string closure of a puncture wound.

One exemplary aspect of the invention is a method of forming a purse string closure at a site of puncture in tissue. The method includes providing a suture applicator having a proximal handle with a length of suture in the handle. A hollow suture needle extends from a distal end of the handle and contains a free end of the length of suture. The suture needle has a distal portion projecting from the handle in a helical shape and terminating in a sharp distal tip. The suture applicator further includes a hollow pivot shaft extending from a distal end of the handle substantially along an axis of the helical distal portion of the suture needle, the pivot shaft having a blunt tip with a substantially larger radial profile than the shaft to prevent puncturing tissue. The method involves providing a puncture needle, passing it through the hollow pivot shaft to extend distally therefrom, and forming a puncture through a heart wall with the puncture needle. A user advances the suture applicator until the blunt tip of the pivot shaft contacts the tissue, and advances and rotates the suture needle so that the sharp distal tip passes helically into tissue around the pivot shaft and continues at least 270° therearound. A free end of the length of suture is directed out of the tissue and grasped. The user then reverses rotation of the suture needle so that it retracts from the tissue while the length of suture remains.

In the aforementioned method, the suture applicator further includes a mechanism (such as a spring) within the handle permitting the pivot shaft to be displaced in a proximal direction relative to the handle but biasing the pivot shaft in a distal direction. The method therefore includes advancing the suture applicator past the point that the blunt tip of the pivot shaft contacts the tissue and displacing the pivot shaft in a proximal direction against the distal bias. The suture applicator further may feature a lock to fix the axial position of the pivot needle, wherein the method includes fixing the axial position of the pivot needle. The handle of the suture applicator may have a chamber housing a suture spool, the length of suture being wound on the spool, whereby the method further includes allowing the length of suture to play off the spool when grasping the free end that emerges from the tissue and reversing rotation of the suture needle so that it retracts from the tissue. The suture needle, the pivot shaft, or both may extend from a distal end of the handle at points that are offset from a longitudinal axis of the handle. The longitudinal axis of the handle may be aligned with a helical axis of a helical suture needle, and the suture needle, the pivot shaft, or both may extend from a distal end of the handle at points that are offset from a longitudinal axis of the handle and thus also offset from the helical axis of the suture needle. In one embodiment, the suture needle extends from the handle at a point offset from the longitudinal axis of the handle, while the pivot shaft extends from a point aligned with the longitudinal axis of the handle.

In one embodiment, the suture needle includes a deflection segment adjacent the distal tip that is more flexible than the rest of the helical distal portion of the suture needle, and the method includes deflecting the deflection segment in a proximal direction to direct the free end of the length of suture back out of the tissue. Alternatively, the suture applicator includes an inner needle arranged to translate through the suture needle and extend from the distal tip thereof, and having a relaxed shape that conforms to the helical shape of the suture needle except at a distal end portion that has a proximal bend so that it deflects in a proximal direction when extended from the distal tip of the suture needle. The method therefore includes translating the inner needle along the suture needle so that the distal end portion extends from the distal tip thereof and deflects in a proximal direction to direct the free end of the length of suture out of the tissue. The inner needle may be hollow with the length of suture extending therethrough, with the method including deflecting the distal end portion of the inner needle out of the tissue and grasping the free end of the length of suture.

In accordance with a specific application of the aforementioned method, the site of puncture is the apex of a ventricle, such as the left ventricle, and the method further includes installing a guidewire through the puncture needle into the ventricle. A second free end of the length of suture is left extending from the point of entry of the suture needle after reversing rotation of the suture needle so that it retracts from the tissue. The user passes a cardiac surgery device along the guidewire and into the ventricle and performs a cardiac surgery with the cardiac surgery device. The user then removes the cardiac surgery device from the heart and applies tension to the first and second free ends of the length of suture to cinch the heart wall tissue and close the puncture.

A further particular cardiac surgery method disclosed herein comprises providing a suture applicator having a proximal handle with a length of suture in the handle. A hollow suture needle extends from a distal end of the handle and contains a first free end of the length of suture, the suture needle having a distal portion projecting from the handle in a helical shape and terminating in a sharp distal tip. A user forms a puncture through a heart wall with a puncture needle and installs a guidewire therethrough. The user advances the suture applicator over the guidewire until the sharp distal tip of the suture needle contacts the heart wall tissue at a point of entry adjacent the puncture. The user advances and rotates the suture needle so that the sharp distal tip passes helically into the heart wall tissue around the puncture and continues at least 270° therearound. The first free end of the length of suture is directed from the heart wall tissue at a point of exit and grasped. The user reverses rotation of the suture needle so that it retracts from the heart wall tissue while leaving a second free end of the length of suture extending from the point of entry. A user passes a cardiac surgery device along the guidewire and into the heart, and performs the cardiac surgery. The cardiac surgery device is then removed from the heart. The user applies tension to the first and second free ends of the length of suture to cinch the heart wall tissue and close the puncture.

In the just-described cardiac surgery method, the suture applicator further may include a hollow pivot shaft extending from a distal end of the handle substantially along an axis of the helical distal portion of the suture needle, the method including advancing the puncture needle through the hollow pivot shaft. The pivot shaft may have a blunt tip with a substantially larger radial profile than the shaft to prevent the blunt shaft from puncturing tissue, with the method including advancing the suture applicator until the blunt tip of the pivot shaft contacts the heart wall tissue. The suture applicator may also include a mechanism (such as a spring) within the handle permitting the pivot shaft to be displaced in a proximal direction relative to the handle but biasing the pivot shaft in a distal direction, whereby the method includes advancing the suture applicator past the point that the blunt tip of the pivot shaft contacts the heart wall tissue and displacing the pivot shaft in a proximal direction against the distal bias. In one embodiment, both the suture needle and the pivot shaft extend from a distal end of the handle at points that are offset from a longitudinal axis of the handle.

The suture needle may include a deflection segment adjacent the distal tip that is more flexible than the rest of the helical distal portion of the suture needle, and the method includes deflecting the deflection segment in a proximal direction to direct the first free end of the length of suture from the heart wall tissue. Alternatively, the suture applicator has an inner needle arranged to translate through the suture needle and extend from the distal tip thereof, the inner needle having a relaxed shape that conforms to the helical shape of the suture needle except at a distal end portion that has a proximal bend so that it deflects in a proximal direction when extended from the distal tip of the suture needle. The user translates the inner needle along the suture needle so that the distal end portion extends from the distal tip thereof and deflects in a proximal direction to direct the first free end of the length of suture from the heart wall tissue. The inner needle may be hollow with the length of suture extending therethrough, wherein the method includes grasping the first free end of the length of suture when the inner needle emerges from the point of exit. In one version, the handle has a chamber housing a suture spool, and the length of suture is wound on the spool, the method including allowing the length of suture to pay off the spool when grasping the first free end and reversing rotation of the suture needle so that it retracts from the tissue. In one application, the site of puncture is the apex of the left ventricle, and the cardiac surgery device includes an introducer sheath carrying a heart valve. In that case, the method may also include performing a heart valve replacement using the introducer sheath extending through the puncture, removing the introducer sheath from the puncture, and tying the first and second free ends of the length of suture to form a purse string closure at the puncture.

In accordance with one structural embodiment disclosed herein, a suture applicator comprises a proximal handle, a length of suture in the handle, and a hollow suture needle extending from a distal end of the handle and containing a free end of the length of suture. The suture needle projects distally from the handle in a helical shape, terminates in a sharp distal tip, and includes a deflection segment adjacent the distal tip that is more flexible than the rest of the helical distal portion of the suture needle.

In accordance with a further structural embodiment disclosed herein, a suture applicator comprises a proximal handle, a length of suture in the handle, and a hollow suture needle extending from a distal end of the handle in a helical shape and terminating in a sharp distal tip. A flexible inner needle extends through the suture needle and is movable therein. The inner needle being hollow and contains a free end of the length of suture. The inner needle has a distal deflection segment that is formed to emerge from the distal tip of the suture needle and angle in a proximal direction.

In accordance with a still further structural embodiment disclosed herein, a suture applicator comprises a proximal handle, a length of suture in the handle, and a hollow suture needle extending from a distal end of the handle in a helical shape and terminating in a sharp distal tip. A flexible inner needle extends through the suture needle and is movable therein. The inner needle is hollow and contains a free end of the length of suture.

In accordance with a still further structural embodiment disclosed herein, a suture applicator comprises a proximal handle having a chamber housing a suture spool, a length of suture partly wound on the spool, and a hollow suture needle extending from a distal end of the handle in a helical shape and terminating in a sharp distal tip, the suture needle containing a free end of the length of suture. The suture needle further has an opening in one side close to the distal tip, the free end of the length of suture extending out of the distal tip and back into the hollow suture needle through the opening.

In accordance with a still further structural embodiment disclosed herein, a suture applicator comprises a proximal handle, a length of suture in the handle, and a hollow suture needle extending from a distal end of the handle in a helical shape and terminating in a sharp distal tip, the hollow suture needle containing a free end of the length of suture. A linear hollow pivot shaft extends from a distal end of the handle substantially along an axis of the helical distal portion of the suture needle, the pivot shaft having a blunt tip with a substantially larger radial profile than the shaft to prevent puncturing tissue. A mechanism within the handle biases the pivot shaft in a distal direction.

In accordance with a still further structural embodiment disclosed herein, a suture applicator comprises a proximal handle, a length of suture in the handle, and a hollow suture needle extending from a distal end of the handle in a helical shape and terminating in a sharp distal tip, the suture needle containing a free end of the length of suture. A puncture needle extends from a distal end of the handle substantially along an axis of the helical distal portion of the suture needle.

In accordance with a purse string suture applicator embodiment disclosed herein, a suture applicator comprises a proximal handle, a length of suture in the handle, and a hollow suture needle extending from a distal end of the handle in a helical shape and terminating in a sharp distal tip, the suture needle containing a free end of the length of suture. A linear hollow pivot shaft extends from a distal end of the handle substantially along an axis of the helical distal portion of the suture needle, the pivot shaft having a blunt tip with a substantially larger radial profile than the shaft to prevent puncturing tissue. A puncture needle extends through the hollow pivot shaft, and a guidewire extends through the puncture needle.

The suture applicator described above may feature a preloaded pledget on the length of suture. Also, the suture may be delivered through the suture needle with a longer solid needle which has the suture crimped at the end of it.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

Features and advantages of the present invention will become appreciated as the same become better understood with reference to the specification, claims, and appended drawings wherein:

DETAILED DESCRIPTION OF THE PREFERRED EMBODIMENTS

Figures 1, 2, 3A:
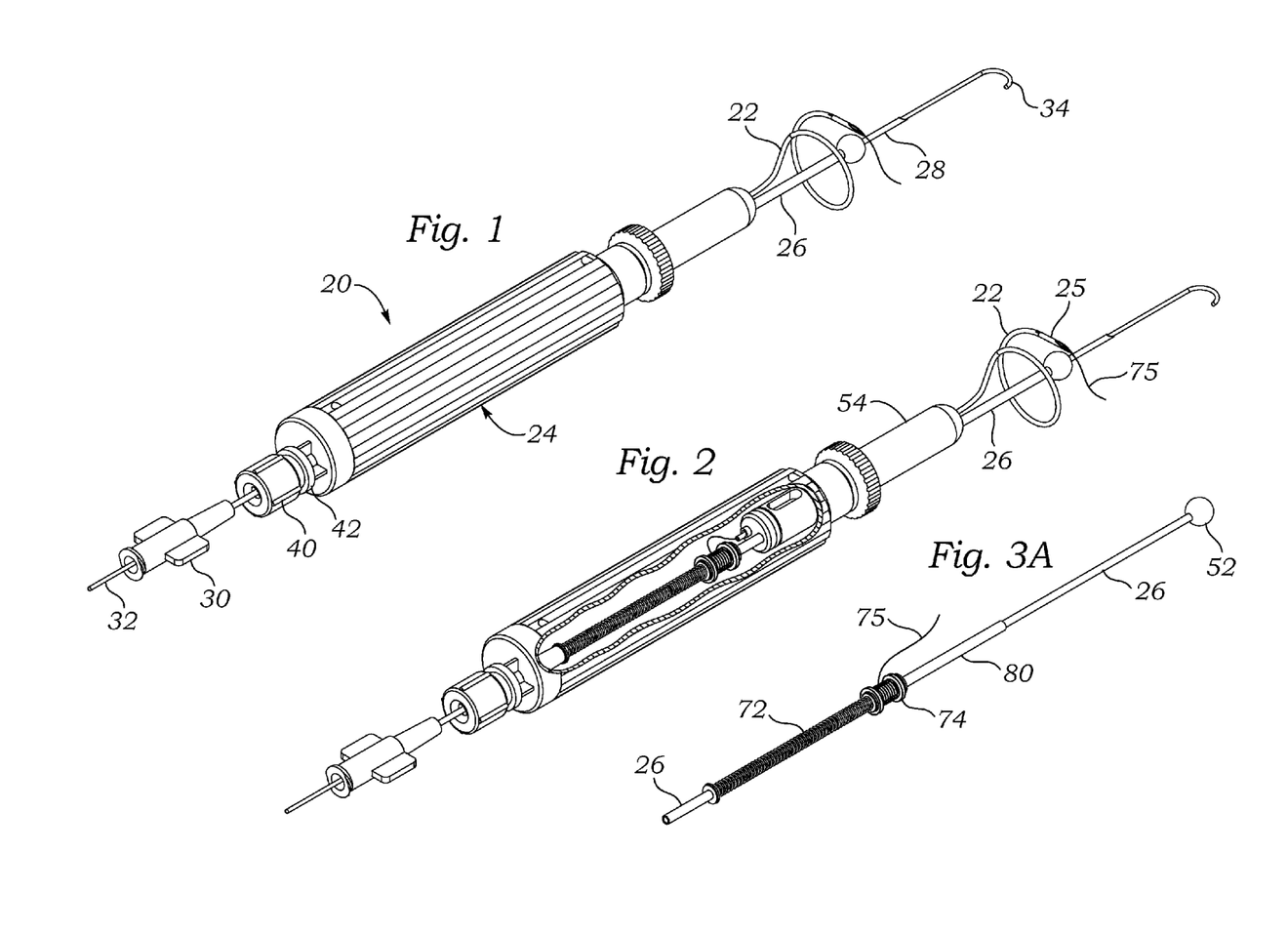
FIG. 1 is a perspective view of one example of an automated purse string suture applicator of the present application having a helical suture needle.
FIG. 2 is a perspective view of the suture applicator of FIG. 1 with a portion cutaway to show internal components.

FIGS. 1 and 2 illustrate an automated purse string suture applicator 20 of the present application having a suture needle 22 extending from a distal end of a handle 24. The handle 24 is shown as generally cylindrical, with the suture applicator 20 defining an elongated instrument. The suture needle 22 is hollow and has a helical shaped portion on a distal length terminating in a sharp distal tip 25. In the context of the present application, the term "helical" refers to a three-dimensional shape that turns around an axis at a constant or varying distance while moving parallel to the axis. A helical shape according to the invention may define at least a partial circle or spiral as viewed along a longitudinal axis, and have an axial component. A "spiral" by one definition is a curve that emanates from a central point, getting progressively farther away as it revolves around the point. However, the rate of change of this outward progression, its magnitude, and likewise the axial component, may vary for different applications and tissue, and no particular values for these parameters should be assigned to the term helical or spiral, per se.

In one application of the invention, a surgeon uses the suture applicator 20 to pre-install a purse-string suture at a location in tissue where a subsequent puncture will be formed for passage of a surgical instrument. In the context of a transapical heart valve procedure, such as a valve replacement, the suture applicator 20 pre-installs one or more purse string sutures in heart tissue at the left ventricular apex. Thus, desirably the suture applicator 20 has the elongated configuration as shown for passage through an intercostal incision, for instance using a mini-thoracotomy. However, in other contexts where greater access to the surgical site is available, the applicator 20 and handle 24 may take other forms such as having a more ergonomic grip.

Figure 3:
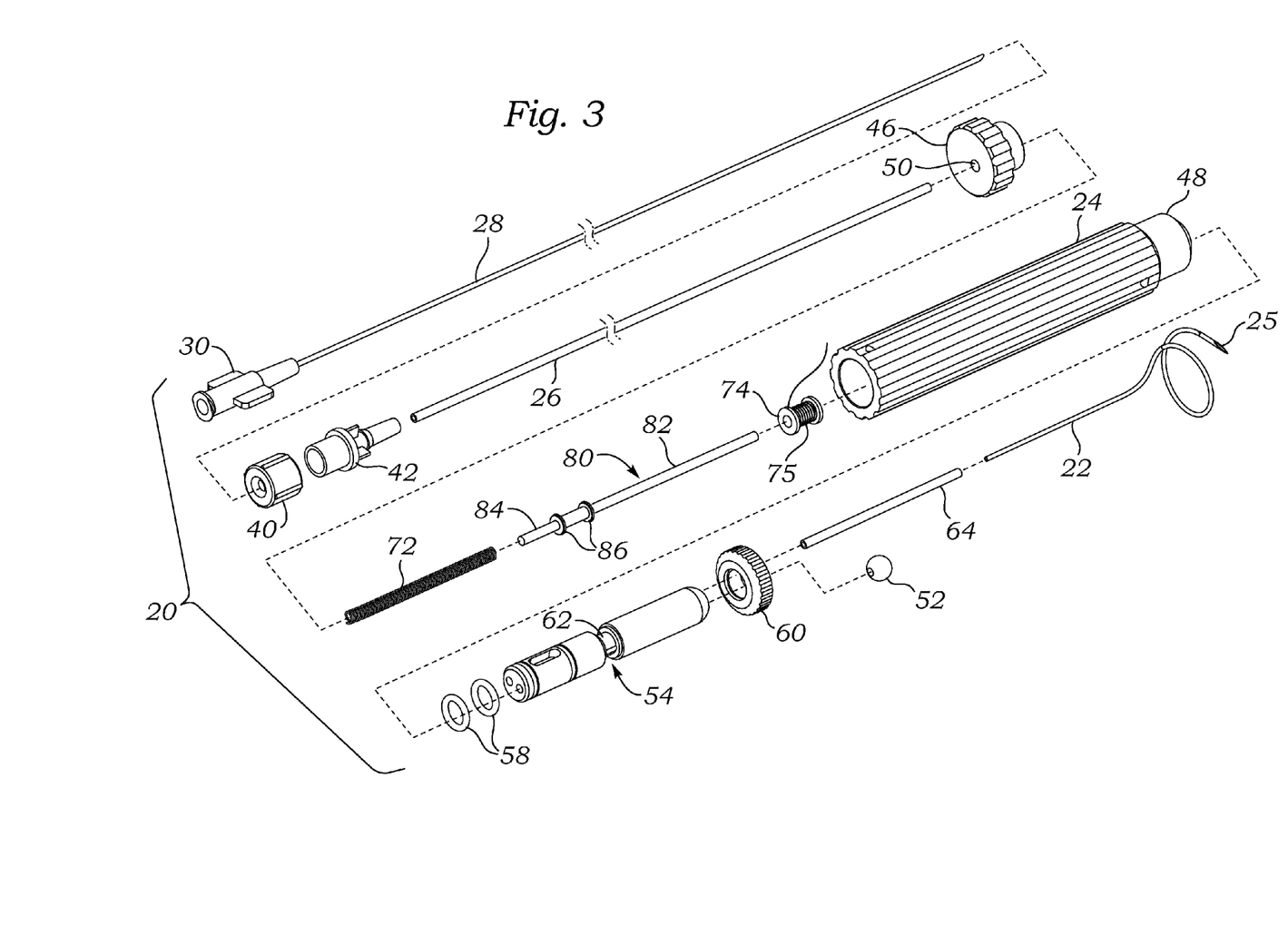
FIG. 3 is an exploded view of the suture applicator of FIG. 1.

With reference still to FIGS. 1 and 2, and also to the exploded view of FIG. 3 and subassembly of FIG. 3A, the suture applicator 20 may also include a pivot shaft 26 having a lumen that receives a needle 28 that slides therein, such as on the distal end of a stylet 30. A guidewire 32 having a J-tip 34 is sized to pass through the needle 28 of the stylet 30, which typically houses a fluid seal therein.

The needle 28 of the stylet 30 extends through a proximal hub 40 that caps a fitting 42, as seen in FIG. 3. The fitting 42 receives and centers the elongated pivot shaft 26 that extends through the handle 24, from a proximal end cap 46 and past a distal end 48. Note that the pivot shaft 26 extends off-center through the tubular handle 24, as shown by the offset aperture 50 in the proximal end cap 46 into which the fitting 42 extends.

A blunt tip 52 mounts on a distal end of the pivot shaft 26. The blunt tip 52 has a substantially larger radial profile than the shaft 26 to prevent puncturing tissue, as will be described. In the illustrated embodiment, the blunt tip 52 is a sphere or ball that mounts by adhesive or interference fit on the distal end of the tubular shaft 26. In one embodiment, the blunt tip 52 is formed of a soft material such as silicone or the like, though a polymer such as Delrin could also be used.

Figure 4:
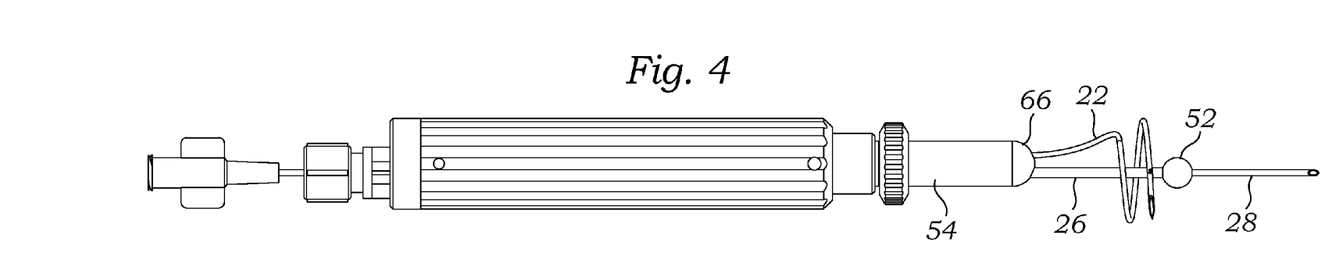
FIGS. 4 and 5 are top and side views of the suture applicator of FIG. 1.
Figure 5:
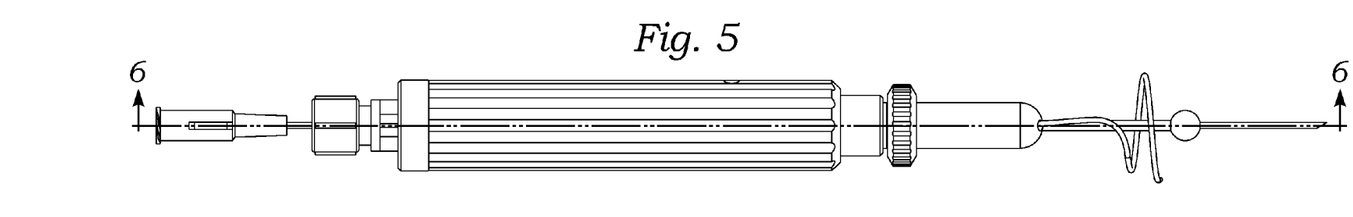
Figure 6:
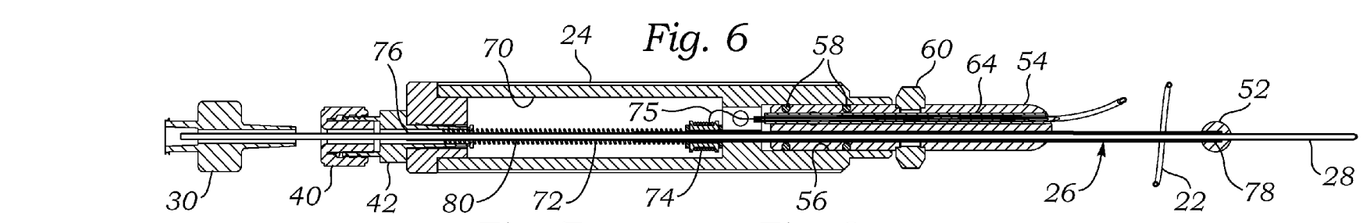
FIG. 6 is a longitudinal sectional view of the exemplary suture applicator taken along line 6-6 of FIG. 5.
Figure 7:
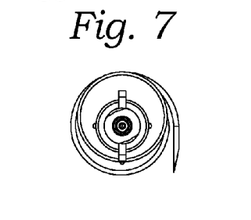
FIGS. 7 and 8 are proximal and distal end views of the suture applicator of FIG. 1.

FIGS. 4-6 also show the offset position of the pivot shaft 26 relative to the handle 24, and through an offset throughbore (not numbered) in a distal bearing cartridge 54. The cartridge 54 fits within a dead-end bore 56 centered at the distal end of the handle 24, constrained by a pair of spaced elastomeric O-rings 58. The bearing cartridge 54 is free to slide longitudinally within a limited travel range in the bore 56. A control ring 60 located around a recessed groove 62 (see FIG. 3) in the cartridge 54 compresses a friction member (not shown) therewithin against the pivot shaft 26, preventing relative longitudinal movement between the cartridge 54 and pivot shaft 26, the purpose of which will be described below.

The cartridge 54 includes a second offset throughbore (not numbered) that receives a tubular sleeve 64 (see also FIG. 3) surrounding a straight proximal length of the suture needle 22. In one embodiment, the sleeve 64 is constrained from movement relative to the cartridge 54, and likewise the suture needle 22 is held within the sleeve 64, so that movement of the cartridge 54 (and coupled handle 24) transmits directly to movement of the suture needle 24. Alternatively, either the sleeve 64 may slide within the cartridge 54 throughbore, or the suture needle 22 slides within the sleeve 64 lumen, so that longitudinal movement of the cartridge 54 is decoupled from that of the suture needle 22. The latter arrangement enables one means of deflecting a distal tip of the suture needle 22, as will be explained below.

Figure 8:
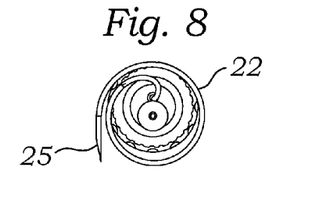

As seen in FIG. 4, the suture needle 22 and the pivot shaft 26 project generally axially from a rounded nose 66 of the cartridge 54, offset from the center of the cartridge. The suture needle 22 relatively quickly transitions between its proximal straight length to the helical distal portion. In the embodiment depicted, the helical distal portion generally circumscribes the axis of the pivot shaft 26, and extends approximately 360° therearound, as seen in the end view of FIG. 8. More particularly, the helical distal portion conforms to an arcuate path around the pivot shaft 26 for about one complete revolution, and terminates in the sharp distal tip 25 on the end of a short linear portion, substantially tangential to the arcuate path. The divergence of the distal tip 25 from the arcuate path of the helical distal portion enables the tip to more easily puncture tissue, and then be directed out of tissue after burrowing through a full circle. In one embodiment, the suture needle 22 is formed from a stainless steel hypotube of about 19 gauge and defines a distal helical path with a taper of about 20° and a diameter of between about 20-25 mm.

With reference again to the subassembly of FIG. 3A and sectional view of FIG. 6, an inner chamber 70 of the handle 24 houses a spring 72 and a spool 74 having a length of suture material 75, both of which mount over the pivot shaft 26. As seen most clearly in FIG. 6, the pivot shaft 26 extends from a proximal end 76 to a distal end 78 at which is mounted the spherical blunt tip 52. A flanged tube 80 is secured on a mid-portion of the pivot shaft 26. The tube 80, as seen in FIG. 3A, has a distal length 82, a shorter proximal length 84, and two circular flanges 86 therebetween. The flanges 86 constrain the suture spool 74, which is free to rotate thereover. The proximal length 84 extends into the distal end of the spring 72, while the pivot shaft 26 continues through the spring to its proximal end within the fitting 42, as seen in FIG. 6. Proximal movement of the pivot shaft 26 (and tube 80) causes the proximal flange 86 to compress the spring 72, thus biasing the blunt tip 52 on the end in a distal direction.

It should be noted that the spool 74 shown retained within the handle 24 mounted for rotation along the longitudinal axis is exemplary only, and the length of suture material 75 may be supplied in other configurations. For instance, a suture spool could be mounted within but perpendicular to the handle, which would necessitate a somewhat larger handle at that location. Alternatively, the spool could be mounted outside the handle 24, either on the handle axis or otherwise.

It will be readily understood that movement of the handle 24 toward tissue eventually brings the blunt tip 52 into contact with the tissue, and a predetermined amount of force may be applied thereto before the spring 72 compresses. This limits the magnitude of force that may be applied to the tissue by the blunt tip 52, and along with its broad shape helps prevent trauma thereto. Furthermore, if movement of the pivot shaft 26 and blunt tip 52 is not desired, the operator may turn the control ring 60 to compress the elastomeric member against the pivot shaft 26. For instance, the surgeon may wish to retract the blunt tip 52 out of the way during the final stages of forming the purse string suture.

Figure 9:
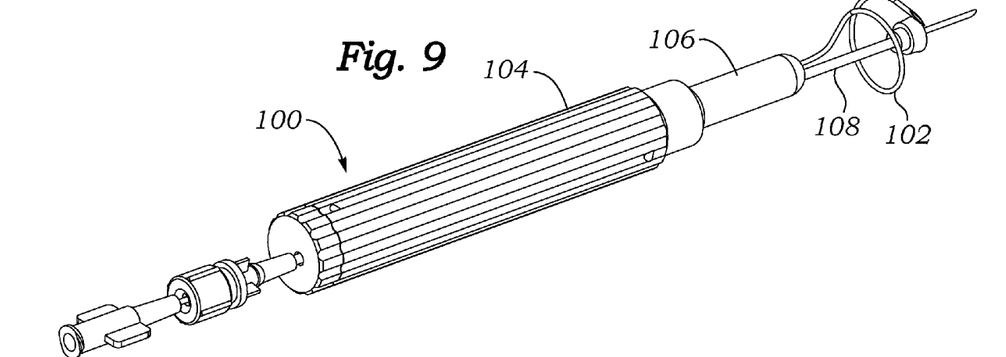
FIG. 9 is a perspective view of an alternative automated purse string suture applicator of the present application having a helical suture needle.
Figure 10:
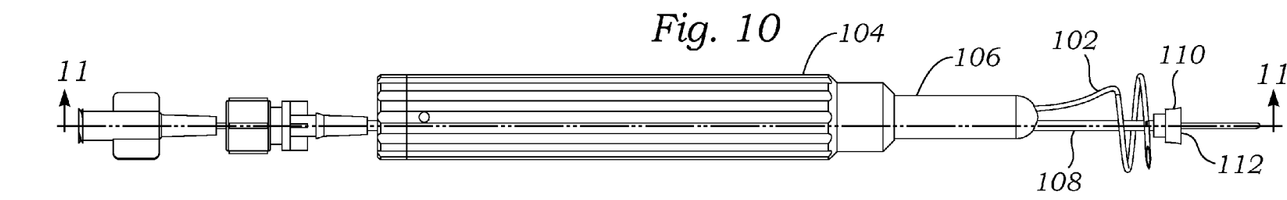
FIG. 10 is a side view of the suture applicator of FIG. 9.
Figure 11:
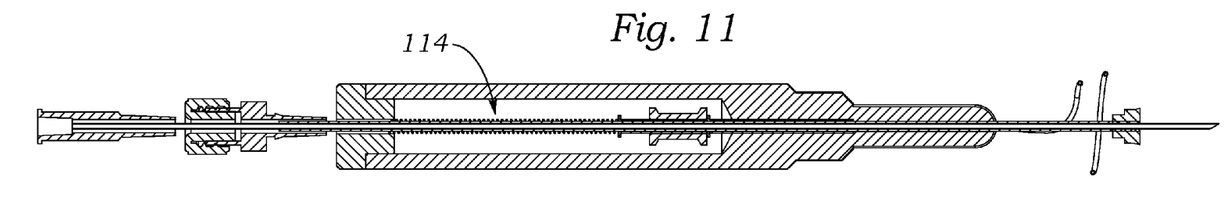
FIG. 11 is a longitudinal sectional view of the alternative suture applicator taken along line 11-11 of FIG. 10.

FIGS. 9-11 are views of an alternative automated purse string suture applicator 100 of the present application having a helical suture needle 102. The suture applicator 100 is in many respects similar to the suture applicator 20 described above, and thus will not be described in such detail. Instead of a cartridge that moves within the handle, a handle 104 projects in a distal nose portion 106. This version does not include a deflectable helical needle, and there is no means for locking the position of a pivot shaft 108 relative to the handle 104.

The pivot shaft 108 terminates in a blunt tip 110, which in this case is shaped as a plunger-shaped element rather than a sphere. A flat distal face 112 of the blunt tip 110 helps maintain the orientation of the handle 104 while installing the purse string suture. The handle 104 contains a spring mechanism 114 as before which biases the pivot shaft 108 and blunt tip 110 in a distal direction, and limits the amount of force that can be applied to tissue by the blunt tip.

Figure 12:
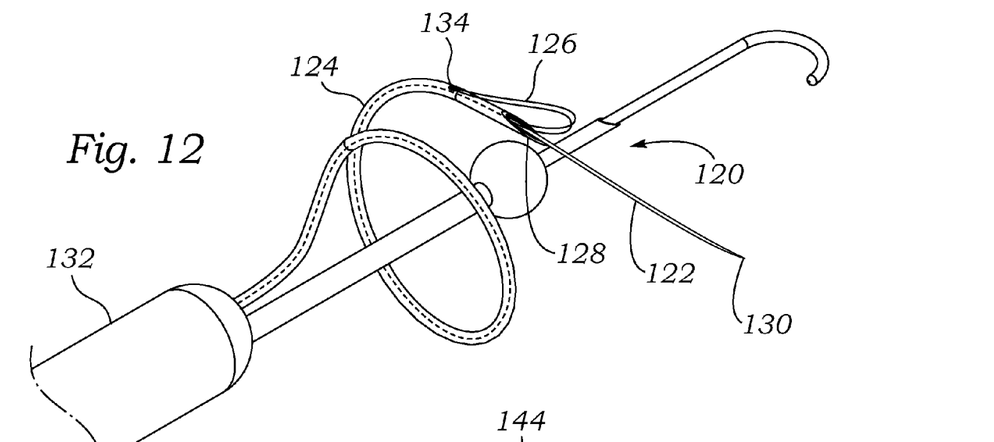
FIG. 12 is a perspective view of a distal end of an exemplary suture applicator disclosed herein having a wire guide extending through the helical suture needle.

FIG. 12 is a perspective view of a distal end of an exemplary suture applicator 120 having a wire guide 122 extending through a helical suture needle 124. The wire guide 122 could be supplied to any of the several suture applicator embodiments described herein.

The helical suture needle 124 is desirably relatively stiff, being formed of a material such as stainless steel or Nitinol, though some forms of the latter may be too flexible such that the helical compresses axially too easily. Because the suture needle 124 is hollow for passage of one or two strands of a length of suture 126, it may not easily pass through fibrous muscle tissue, such as at the left apex of the heart. Therefore, a solid thin wire guide 122 may be inserted into the lumen of the suture needle 124 and extended out the sharp distal tip 128. Due to its flexibility it may be selectively retractable through the suture needle 124, or may be fixed in place. A sharp tip 130 provides a leading end for the assembly to facilitate passage of the larger suture needle 124 through tissue.

FIG. 12 also illustrates an embodiment of an arrangement of the length of suture 126 at the distal tip 128 of the suture needle 124. In particular, a double strand of the length of suture 126 extends from the proximal handle 132 and exits the sharp distal tip 128. The double suture strand 126 then curls back on itself and enters a small opening 134 in one side of the suture needle 124 close to the distal tip 128. In this way, the free end of the length of suture 126 (in this case the free end of the double strand) is held in place and will not migrate proximally down the hollow suture needle 124.

Figure 13A:
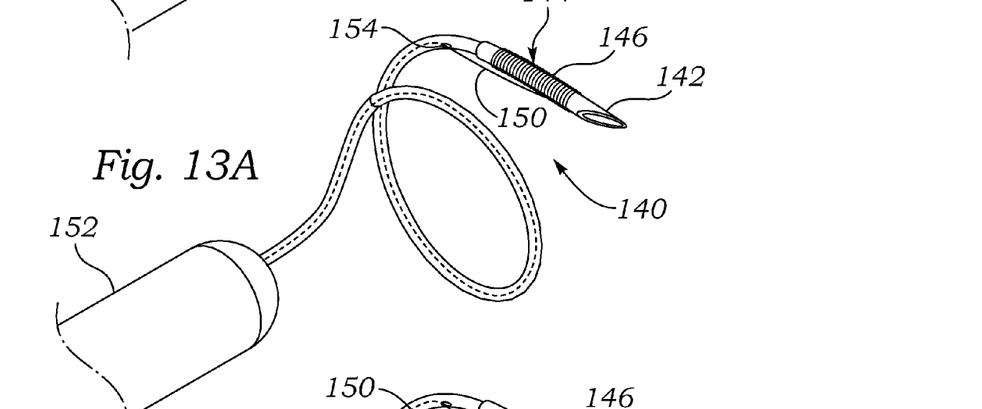
FIGS. 13A and 13B are perspective views of a further exemplary suture applicator having a helical suture needle with a deflectable tip.
Figure 13B:
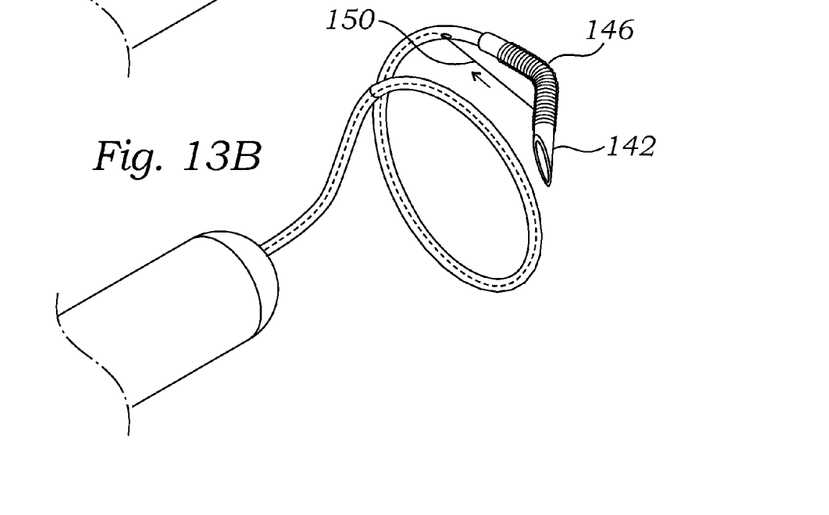

FIGS. 13A and 13B illustrate a helical suture needle 140 with a deflectable tip which may be incorporated into any of the suture applicators described herein. The hollow suture needle 140 terminates in a sharp distal tip 142 as before, and includes a deflection segment 144 adjacent thereto that is more flexible than the rest of the helical distal portion of the needle. In one embodiment, the deflection segment 144 is provided by a short tube formed partly in a coil spring 146. A deflection wire or filament 150 extends from a proximal handle 152 through the lumen of the suture needle 140 and exits through an opening 154 just proximal to the coil spring 146, and on a side closest to the handle 152. The deflection filament 150 then attaches to a point just distal to the coil spring 146, also on the side closest to the handle 152. Pulling the filament 150 in the direction of the arrow in FIG. 13B causes deflection of the sharp distal tip 142, thus facilitating redirection of the tip (and suture therein) out of the tissue.

It should be understood that there are a number of ways to direct the suture out of tissue, and the deflectable tip embodiment illustrated in FIGS. 13A-13B is just one example. Furthermore, there are a number of ways to actuate a pull wire from the proximal handle 152. As explained above with reference to FIGS. 1-8, a cartridge 54 movable with respect to the handle 24 may be provided, with one end of a deflection filament connected to the cartridge. By displacing the cartridge 54 in a proximal direction the deflection filament is pulled proximally through the suture needle 22, which can be provided with a deflectable segment. More specifically, the control ring 60 deflects the needle tip when being pushed, and the needle tip straightens out when the control ring 60 is pulled back to the original position. The control ring 60 may have stop control for this push/pull movement.

Another feature for the control ring 60 is that it actuates a cam lock mechanism (the cam component is not shown) to lock the spring-loaded pivot shaft 26 when being turned or twisted from 90 to 150 degrees clockwise. The pivot shaft 26 would be released when the control ring 60 is turned in the opposite direction.

Figure 14A:
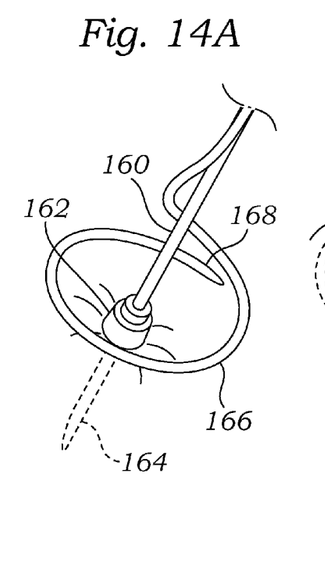
FIGS. 14A-14D are perspective views of operation of a suture applicator as disclosed herein forming a purse-string suture in heart tissue.
Figures 14B, 14C:
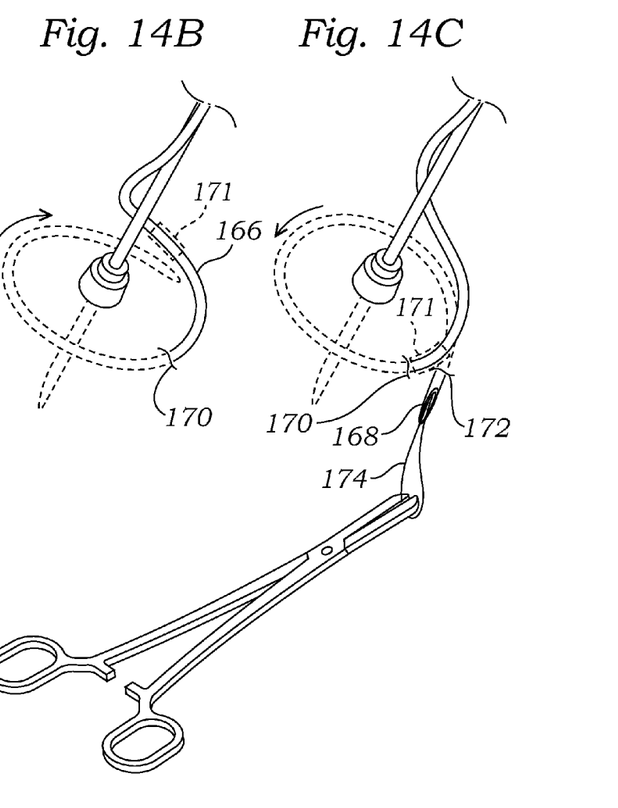

FIGS. 14A-14D are perspective views of operation of a suture applicator of the present application forming a purse-string suture in heart tissue. A pivot shaft 160 having a blunt tip 162 is first brought into contact with tissue. A puncture needle 164 may or may not be advanced into the tissue prior to formation of the purse string suture. The surgeon advances a helical suture needle 166 toward the tissue surface and rotates the needle (clockwise as in FIG. 14B) to cause the sharp tip 168 to puncture the tissue. FIG. 14B shows the sharp tip after having rotated at least about 270° from the point of entry 170. It should be understood that, depending on the particular embodiment, the suture needle 166 may advance nearly an entire revolution around the pivot shaft 160, or in a further embodiment may advance at least three-quarters of the way around. In this way, tension on the free ends of the suture cinches the tissue within the loop formed thereby. However, the needle 166 may rotate more than a full revolution while still forming a purse string suture, and the extent to which the suture passes through tissue, is within certain bounds, a surgeon's preference.

As will be described further below, a rotation stop member 171 may be provided on the suture needle 166 to indicate when a full revolution of the needle in the tissue has been met, at which point the user knows to stop screwing the needle farther in. The stop member 171 is shown as a band of material around the outside of the suture needle 166 that provides a visual indication of the full revolution and also impedes further advancement of the needle into the tissue at that extent of rotation. In one embodiment, the stop member 171 comprises extruded plastic or elastomeric tubing. Another option is to provide an indicator marking on the suture needle 166, such as a printed or inscribed band, in place of the stop member 171 to provide a purely visual reference for the user of one full rotation of the needle 166.

Eventually, a full rotation of the needle 166 has occurred, indicated for example by the stop member 171 approaching or contacting the point of entry 170, at which point the sharp tip 168 is directed out of the tissue at a point of exit 172, as in FIG. 14C. Advantageously, the stop member 171 presents a highly visible marker to aim for when directing the sharp tip 168 out of the tissue. The location of the stop member 171 around the suture needle 166 is approximately one full revolution from the tip 168, looking along the axis of the helical needle, though the two elements are offset axially. If the tip 168 emerges at the point of exit 172 close to the point of entry 170, which is easily visible by the presence of the stop member 171, then the resulting purse string suture circumscribes about a full circle. The stop member 171 arrests further movement of the needle 166 and helps the user avoid under- or over-shooting the closure, which ensures a tight circular knot (or closure). The closure may extend at least 270° around, up to about 360° around, or even more than 360° around.

There are a number of ways to cause the tip 168 to emerge from the tissue, including simply angling the entire instrument to direct the tip in a proximal direction. However, if the tissue is somewhat fragile, as in older patients, a wire guide or deflection mechanism may be provided to assist the redirection of the tip 168. In one embodiment, the tip deflects upward out of the tissue into the position of FIG. 14C. More generally, it is the free end of the suture material 174 that must emerge from tissue, and the present application discloses a number of ways to accomplish that, including techniques in which the sharp tip 168 remains embedded.

Subsequently, the surgeon grasps the free end (or double strand) of suture material 174 with forceps or the like, as shown in FIG. 14C. While holding the suture 174, the suture needle is rotated in the opposite direction (counter-clockwise as in FIG. 14C) to reverse its path through the tissue. The length of suture 174 pays out from the spool (such as at 74 in FIG. 6).

Figure 14D:
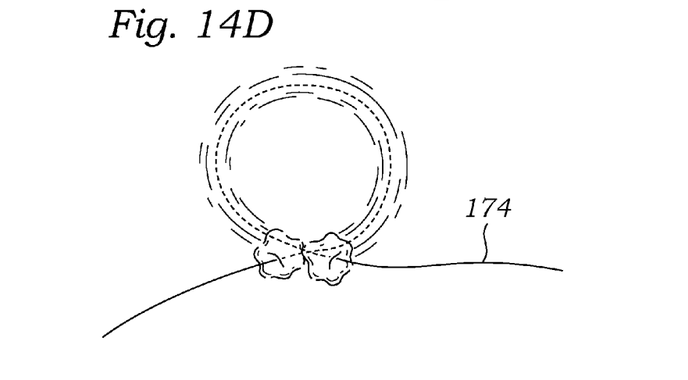

Finally, the suture applicator has been completely removed and two free ends of suture, or double-stranded suture, extend from the entry and exit points 170, 172. A puncture through the middle of the suture loop can then be formed for passage of surgical instruments such as dilators, introducers, catheters and the like. Tension on the free ends of suture 174 provides a fluid seal around these instruments. After the procedure is carried out, pledgets may be added to the free ends which are then pulled tight and knotted to close the puncture wound.

Figure 15A:
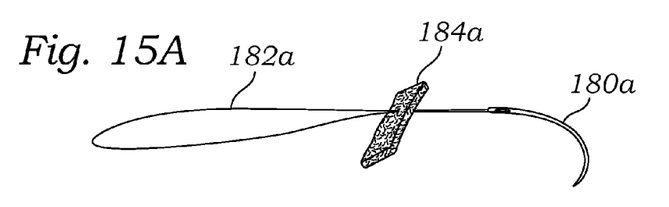
FIGS. 15A and 15B illustrate two lengths of double strand sutures with needles having pledgets pre-installed thereon.
Figure 15B:
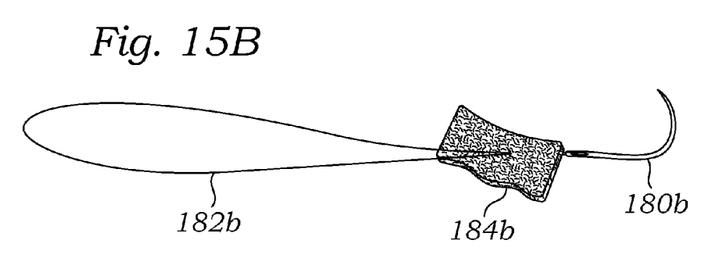

One technique that may be used to facilitate loading of a suture applicator as disclosed herein is to pre-attach pledgets onto the lengths of suture material. FIGS. 15A and 15B each show a shaped needle 180a, 180b having a dual strand of suture 182a, 182b thereon. A pledget 184a, 184b may be pre-installed on each strand of suture 182a, 182b. The pledgets 184a, 184b are then deployed at point of insertion (i.e., prior to passing the suture applicator needle therethrough) and then as the suture applicator needle exits out of the tissue. This causes the shaped needle to pass through the pledgets and so will the length of suture within the applicator. The same pledget is loaded over the shaped needle tip prior to removing/grabbing the suture.

Figure 16:
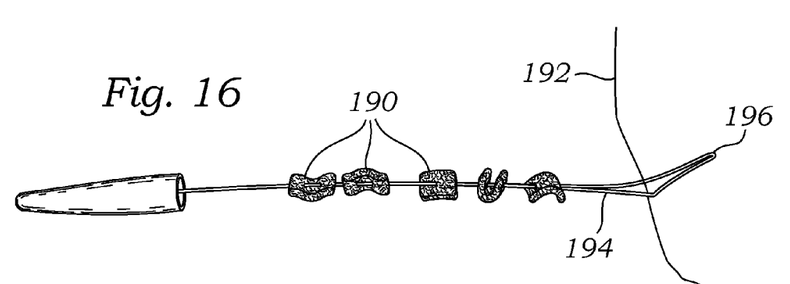
FIG. 16 shows a device loading a pledget onto a length of suture material.

FIG. 16 shows a device for attaching pledgets 190 to a length of suture 192. The device has a looped wire 194 bent into a sharp end 196 which can be threaded through a number of pledgets 190. The length of suture material 192 can then easily pass though the looped wire 194 and a pledget 190 loaded over its mid-portion.

Figure 17:
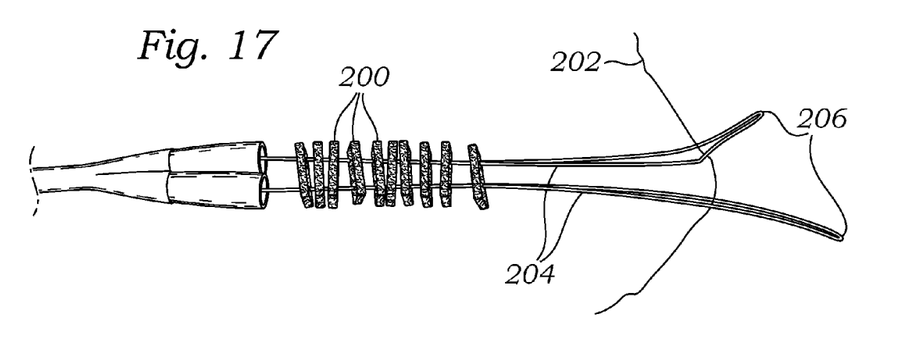
FIG. 17 shows a device loading a pledget onto two lengths of suture material at the same time.

FIG. 17 shows another device for attaching pledgets 200 to two lengths of suture 202 at the same time. The device has two looped wires 204 each bent into a sharp end 206 which can be threaded through a number of pledgets 200. A length of suture material 202 can then easily pass though both looped wires 204 and a pledget 200 loaded over both ends. A handle facilitates gripping, and the device is 5-6 inches long maximum.

Figures 18A, 18B:
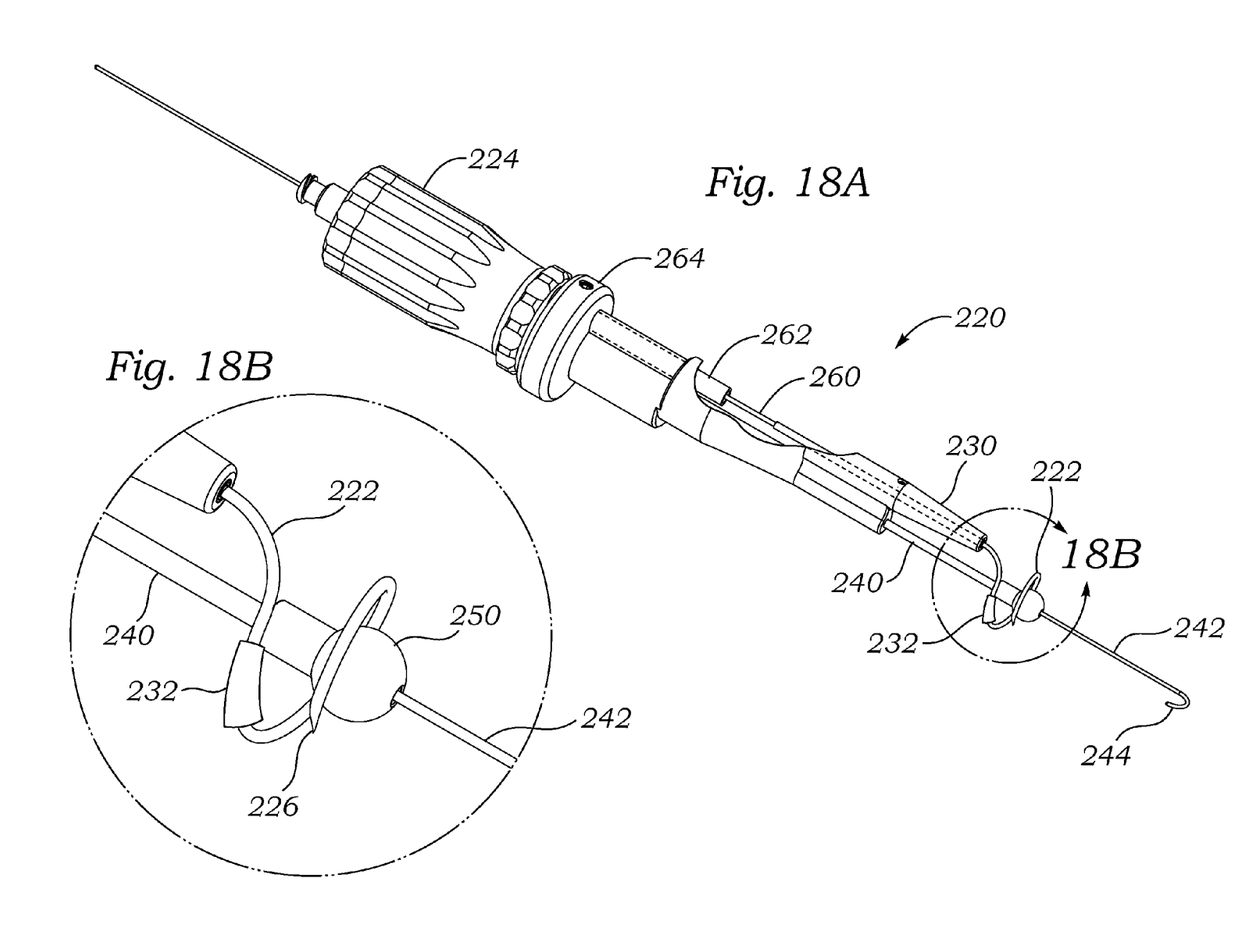
FIG. 18A is a perspective view of an alternative automated purse string suture applicator of the present application having a helical suture needle housing an inner deflectable needle.
FIG. 18B is an enlarged view of a distal end of the suture applicator of FIG. 18A.

The present application previously described a device that articulates the corkscrew needle and re-directs it above the tissue surface after "screwing" it in. FIG. 18A shows an alternative automated purse string suture applicator 220 of the present application which utilizes a deflectable needle within a helical suture needle 222 to direct a distal tip and free end of the suture upward out of tissue. Instead of the deflectable helical suture needle 140 of FIG. 13A, the corkscrew needle 222 of FIG. 18A has another smaller needle coaxially placed inside as an inner needle 260, which may be made from a high elasticity material such as Nitinol. The inner needle 260 may be formed generally in same shape as the corkscrew needle, so as to slide more easily therein, but about 1 inch at the distal end would have a curve upward at about 90 degrees.

The suture applicator 220 combines elements of the suture applicator 120 having a wire guide 122 shown in FIG. 12 with the deflectable tip of the helical suture needle 140 of FIGS. 13A and 13B. That is, rather than deflecting the entire suture needle 222, a smaller inner needle 260 extends therethrough as a wire guide of sorts and deflects upward from the tissue upon advancement from the end 226 of the suture needle 260.

The suture applicator 220 includes the helical suture needle 222 extending from a distal end of a handle 224. As in previous embodiments, the suture applicator 220 defines an elongated instrument with a generally cylindrical handle 224. The suture needle 222 is hollow and has a helical or corkscrew-shaped portion on a distal length terminating in a sharp distal tip 226, as best seen in the enlarged view of FIG. 18B. The needle 222 extends distally from a generally tubular or slightly conical sleeve 230 that projects from a main body of the handle 224. The sleeve 230 defines therein a throughbore that receives and holds fixed a straight proximal portion of the helical suture needle 222. As will be described, the helical suture needle 222 remains stationary both axially and rotationally with respect to the handle 224, while the inner needle 260 slides axially therethrough. A tubular stop member 232 extends around the suture needle 222 and functions as a rotation indicator, described below. The stop member 232 may comprise a portion of extruded plastic or elastomeric tubing, or may alternatively be an indicator marking on the suture needle 222, such as a printed or inscribed band. In the illustrated embodiment, the stop member 232 comprises a short length of tubing surrounding the suture needle 222, and may have a slightly conical profile to present a wider distal end that more effectively halts advancement of the suture needle and provides clear tactile feedback to the user. Also, the stop member 232 may be provided in a bright color, such as yellow, to be more distinctive against the typically red tissue of the heart wall.

With reference still to FIG. 18A, the suture applicator 220 also includes a pivot shaft 240 having a lumen that receives a needle (not shown), such as on the distal end of a stylet 30 described above. A guidewire 242 having a J-tip 244 passes through the stylet, and typically remains advanced through the suture applicator 220 during the suturing procedure. In one embodiment, the shaft 240 may accommodate guidewires with diameters up to about 0.050".

In one application, a surgeon uses the suture applicator 220 to pre-install a purse-string suture at a location in tissue where a subsequent puncture will be formed for passage of a surgical instrument. In the context of a transapical heart valve procedure, such as a valve replacement, the suture applicator 220 pre-installs one or more purse string sutures in heart tissue at the left ventricular apex. Thus, desirably the suture applicator 220 has the elongated configuration as shown for passage through an intercostal incision, for instance using a mini-thoracotomy. Further, the stylet (not shown) forms a small puncture and access passage through the heart wall so that the guidewire 242 may be advanced into the left ventricle and farther to the valve implant location, e.g., the aortic annulus. The guidewire 242 remains in place even after the purse string suture is pre-installed to guide subsequent instruments, such as a balloon catheter, to the implant location.

A cushion ball (or a hemisphere) 250 attaches to the tip of pivot shaft 240 to reduce damage to the heart tissue while deploying the device. Moreover, a spring 252 (see FIG. 19A) within the handle 224 biases the shaft 240 distally so that after the ball 250 contacts the exterior of the heart wall, it retracts toward the handle 224 when greater forward pressure is applied. The spring mechanism may be similar to that shown above with respect to the spring 72 in FIG. 6.

Figures 19A, 19B:
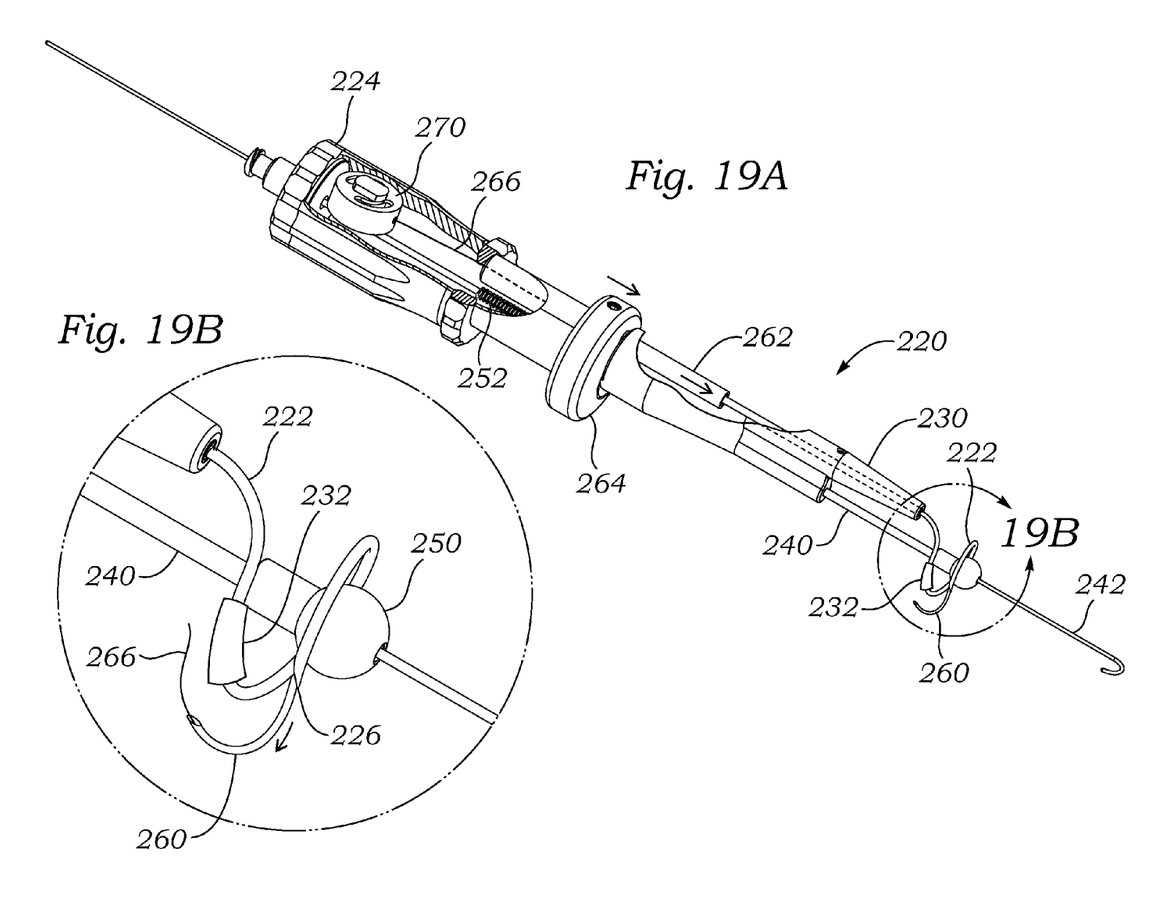
FIG. 19A is a perspective view of the suture applicator of FIG. 18A showing deployment of the inner deflectable needle from the end of the helical suture needle.
FIG. 19B is an enlarged view of a distal end of the suture applicator of FIG. 19A.

FIGS. 19A and 19B show deployment of an inner deflectable needle 260 from the sharp distal tip 226 of the helical suture needle 222. An elongated slider 262 arranged to move axially within the handle 224 connects to a proximal end of the inner needle 260. A slider ring 264 that moves over the outside of the handle 224 and secured to the slider 262 helps push and pull the slider easily by thumb action. Of course, the slider ring 264 may take many forms, such as a lever, trigger, tab slider, etc. A spring-biased ball plunger (not shown) or other such detent-like lock may be embedded in the slider ring 264 to momentarily lock the slider in place in a retracted position, in which the inner needle 260 is retracted inside the corkscrew needle 222. This temporary lock prevents the inner needle 260 from accidentally being pushed forward while the user deploys the corkscrew needle 222.

With the ball plunger lock unlocked, or with sufficient distally-applied pressure to overcome the ball plunger lock, the slider ring 264 can be distally moved to displace the slider 262 and inner needle 260 forward, so that the inner needle projects from the distal tip 226 of the helical suture needle 222, as seen best in FIG. 19B. In one embodiment, the inner needle 260 generally has a relaxed or "normal" shape that conforms to the helical shape of the suture needle 222, except at a distal end portion that has a relaxed shape with a proximal bend as shown. Again, the inner needle 260 is desirably formed from a highly flexible memory material such as Nitinol to permit it to snake easily through the suture needle 222.

Since the inner needle has to be moved back and forth to retract within the corkscrew needle and forward out of the tissue respectively, the vertical axial of corkscrew needle is shaped in a gradual curve so that it makes the advancement and retraction movements easier and smoother.

In this embodiment, the inner needle 260 is hollow and carries a length of suture 266 to the end of the suture needle 222 and feeds it back in a proximal direction when desired. One end of a length of suture protrudes out of or is otherwise carried by the distal end of the inner needle 260, while the other end wraps around a suture spool 270 housed within the handle 224. The suture spool 270 is contained inside the handle for convenience and better control or maneuverability of the device, though it could be outside the handle such as at a proximal end, or a free length of suture could simply dangle from the proximal end of the device.

In order to deploy the device the inner needle 260 has to be retracted inside the corkscrew needle 222. To do so, the user pulls back the slider ring 264 and locks it in place before deploying the device through the heart tissue. The user places the pivot shaft 240 of the suture applicator 220 over the guide wire 242 and advances the ball 250 thereon into contact with the tissue, such as at the apex of the left ventricle. The user then places the sharp distal tip 226 of the corkscrew needle 222 into contact with the tissue. At this point, clockwise rotation of the entire handle 224 about the pivot shaft 240 causes the distal tip 226 to pierce the tissue and start to "screw" downward, embedding itself. As the corkscrew needle 222 penetrates the tissue by pushing and turning the handle 224 clockwise, the spring-loaded pivot shaft 240 retracts due to its spring-biased mount within the handle 224, thus avoiding perforating through the heart wall while still maintaining the center of the corkscrew needle's movement.

At a specific point as marked on the corkscrew needle 222 (or by a feature such as the tubular stop member 232 on the needle 222), the user halts the corkscrew movement. The user then advances the inner needle 260 by displacing the slider ring 264 distally along the handle 224. This action drives/directs/deflects the distal portion of the inner needle 260 out of the end of the corkscrew needle 222. Because of the bent relaxed shape of the distal portion of the inner needle 260, the inner needle 260 angles upward proximally to break through and emerge from the tissue surface. The free end of the length of suture can be grabbed and secured outside of the tissue, while the user retracts the inner needle 260 and "unscrews" the helical suture needle 222 from within the tissue. Two opposing free ends of the length of suture are thus available for cinching the embedded loop in a purse string closure. Pledgets as described above may also be pre-installed on the length of suture to speed up the process and help avoid cutting the tissue when tightening the suture.

One surgical procedure that may utilize the devices of the present application is a transapical heart valve replacement through the left ventricular apex, as disclosed in U.S. Patent Publication No. 2007-0112422 to Dehdashtian, filed Nov. 16, 2005, and in U.S. Provisional Application No. 61/220,968 to Pintor, filed Jun. 26, 2009, the disclosures of which are expressly incorporated herein by reference. First, the prosthetic heart valve and various delivery instruments are selected and prepared for use by removing them from any packaging and rinsing or sterilizing as needed. The prosthetic heart valve is then crimped over the balloon on the catheter.

Next, the surgeon installs one or more purse-string sutures in the tissue of the left ventricular apex surrounding prior to or just after formation of an initial puncture using the devices disclosed herein. One advantage of the system described herein is the provision of the puncture needle and guidewire in the device itself. This greatly improves ease of use because the penetration or puncture needle and guidewire can be loaded within the handle prior to use. The operation of the system thus accomplishes both installing the guidewire and the purse string suture, two important preparatory steps in a number of different cardiac surgeries.

In one embodiment, the surgeon places a first line of purse-string sutures generally in a first circle in one direction, and then places a second line of purse-string sutures generally in a circle concentric to the first circle but in an opposite direction. A single device disclosed herein may be used to form both purse string sutures, or two devices pre-loaded with suture material can be used. The result is two concentric circles of separate purse-string sutures defining a periphery within which the puncture is formed, or was already made.

The purse-string sutures can therefore be pulled to cinch the ventricular tissue around whatever object passes through the puncture. In particular, the purse-string sutures are tightened around both a guidewire and introducer sheath. Installing the separate lines of purse-string sutures in opposite directions helps prevent tearing of the ventricular tissue and provides a more uniform compression about whatever elongated object passes through the puncture.

If not already installed, the surgeon introduces a guidewire through the apical puncture in the left ventricle LV and within the purse string sutures, through the native aortic valve AV and into the ascending aorta AA. A pre-dilation step of the annulus may be performed to enlarge or crack existing calcification in the aortic annulus. The surgeon then inserts a dilator and introducer sheath into the LV through the apical puncture as an access port.

The balloon catheter is advanced over the guidewire and through the introducer sheath. The surgeon locates the prosthetic heart valve at the aortic annulus and between the native aortic leaflets. Radiopaque markers may be provided on the distal tip of the introducer sheath to more accurately determine its position relative to the valve and balloon. When the surgeon is satisfied of the proper positioning and rotational orientation of the valve, the balloon is expanded into contact with the annulus. During these steps, the pre-formed purse string suture(s) may be used to apply tension to the exterior of the introducer sheath (or any other device used in the cardiac procedure) for sealing purposes.

The surgeon then deflates the balloon and withdraws the entire delivery system including the balloon catheter over the guidewire. The introducer sheath is withdrawn, followed by the guidewire. Ultimately, the purse-string sutures previously described are cinched tight and tied to close the puncture, as seen in FIG. 14D.

The exemplary procedure may be performed as a first time valve implant or to supplement a previous implant. A relatively large proportion of recipients of prosthetic heart valves are older, typically older than 60. Over time, prosthetic heart valves have been known to show reduced performance and even failure. Re-operating on septuagenarians and even octogenarians is problematic. However, a port access procedure such as disclosed herein eliminates open-heart surgery and potentially cardiopulmonary bypass, and is therefore more desirable for the aging patient. Therefore, the present invention contemplates transapical implantation of a prosthetic heart valve over an existing prosthetic valve implant. In such a case, a pre-dilation step is typically not necessary, though it is conceivable.

The prosthetic heart valve implantation procedure described herein may be performed in conjunction with cardiopulmonary bypass, or without bypass in a so-called off-pump procedure. The necessity for bypass depends on a number of factors, including the patient's age, vulnerability to such a procedure, and viability of the native leaflets. Ideally, the implantation procedure is performed off-pump.

While the invention has been described in various embodiments, it is to be understood that the words which have been used are words of description and not of limitation. Therefore, changes may be made within the appended claims without departing from the true scope of the invention.

What is claimed is:

1. A suture applicator, comprising;
    a proximal handle;
    a length of suture;
    a hollow suture needle extending from a distal end of the handle, the hollow suture needle comprising a helical distal portion and a distal end, the hollow suture needle further comprising a deflection segment positioned at the distal end, wherein the deflection segment extends proximally, with respect to the suture applicator, from the distal end of the hollow suture needle, wherein the deflection segment is configured to deflect from a first shape generally in helical alignment with the helical distal portion to a second shape wherein the deflection segment is deflected to extend proximally toward the handle;
    wherein the length of suture passes through the hollow suture needle to the deflection segment.

2. The suture applicator of claim 1, wherein the deflection segment is more flexible than the rest of the hollow suture needle.

3. The suture application of claim 2, further comprising: a deflection mechanism configured to deflect the deflection segment from the first shape to the second shape.

4. The suture applicator of claim 3, wherein the deflection mechanism comprises a deflection wire that extends from the proximal handle through a lumen of the hollow suture needle and exits through an opening in the hollow suture needle just proximal to the distal end and on a side closest to the handle.

5. The suture applicator of claim 1, wherein the helical distal portion defines a helical axis, and the suture applicator further comprises:
    a pivot shaft extending distally from the handle, the pivot shaft extending through the helical distal portion in longitudinal alignment with the helical axis of the helical distal portion.

6. The suture applicator of claim 1, wherein the deflection segment comprises a short tube formed partly in a coil spring.

7. The suture applicator of claim 6, wherein the deflection mechanism comprises a deflection wire that extends from the proximal handle through a lumen of the hollow suture needle and exits through an opening in the hollow suture needle just proximal to the distal end and on a side closest to the handle and attaches to a point just distal to the coil spring, also on the side closest to the handle.

8. The suture applicator of claim 1, wherein the proximal handle comprises a chamber housing a suture spool, and wherein a proximal portion of the length of suture is at least partly wound onto the suture spool.

9. The suture applicator of claim 1, further comprising:
    a linear hollow pivot shaft extending from a distal end of the handle substantially along a helical axis of the helical distal portion of the hollow suture needle, the pivot shaft having a blunt tip with a substantially large radial profile to prevent puncturing of tissue by the pivot shaft; and
    a mechanism within the handle biasing the pivot shaft in a distal direction.

10. The suture applicator of claim 9, further comprising:

a puncture needle extending through the linear hollow pivot shaft, the puncture needle having a sharpened distal tip configured to puncture tissue.

11. The suture applicator of claim 10, further comprising:

a guidewire extending through the puncture needle.

12. A suture applicator, comprising;

a proximal handle;

a length of suture;

a hollow suture needle extending from a distal end of the handle, the suture needle projecting distally from the handle and having a helical distal portion terminating in a sharp distal tip;

a flexible inner needle extending through the suture needle and being movable therein, the inner needle being hollow and containing a distal portion of the length of suture, the inner needle including a distal deflection segment that is formed to emerge from the distal tip of the suture needle and angle in a proximal direction;

a linear hollow pivot shaft extending from a distal end of the handle substantially along a helical axis of the helical distal portion of the suture needle, the pivot shaft having a blunt tip with a substantially large radial profile to prevent puncturing of tissue by the pivot shaft; and a mechanism within the handle biasing the pivot shaft in a distal direction; and a puncture needle extending through the linear hollow pivot shaft, the puncture needle having a sharpened distal tip configured to puncture tissue.

13. The suture applicator of claim 12, further comprising:

a guidewire extending through the puncture needle.

* * * * *